(12) United States Patent
Bryan et al.

(10) Patent No.: US 9,365,490 B2
(45) Date of Patent: Jun. 14, 2016

(54) METHOD OF MAKING A TEMPLATING AGENT

(71) Applicant: Johnson Matthey PLC, London (GB)

(72) Inventors: Richard Charles Bryan, Lancaster (GB); Ronald Henry Jones, Carnforth (GB); Nigel Robinson, Morecambe (GB)

(73) Assignee: Johnson Matthey PLC, London (GB)

( * ) Notice: Subject to any disclaimer, the term of this patent is extended or adjusted under 35 U.S.C. 154(b) by 47 days.

(21) Appl. No.: 14/227,222

(22) Filed: Mar. 27, 2014

(65) Prior Publication Data

US 2014/0296573 A1     Oct. 2, 2014

Related U.S. Application Data

(60) Provisional application No. 61/805,654, filed on Mar. 27, 2013.

(51) Int. Cl.
*C07C 209/68* (2006.01)
*C07C 209/00* (2006.01)

(52) U.S. Cl.
CPC ............. *C07C 209/68* (2013.01); *C07C 209/00* (2013.01)

(58) Field of Classification Search
None
See application file for complete search history.

(56) References Cited

U.S. PATENT DOCUMENTS

| 2,635,100 | A | * | 4/1953 | Werntz ........................ 544/65 |
| 4,859,442 | A | | 8/1989 | Zones et al. |
| 8,163,951 | B2 | | 4/2012 | Szarvas et al. |
| 8,252,943 | B2 | | 8/2012 | Szarvas et al. |
| 2012/0010431 | A1 | | 1/2012 | Wigbers et al. |

FOREIGN PATENT DOCUMENTS

WO     2010103062 A1     9/2010

OTHER PUBLICATIONS

Maurizio Selva et al.; Green Chemistry Metrics: A Comparative Evaluation of Dimethyl Carbonate, Methyl Iodide, Dimethyl Sulfate and Methanol as Methylating Agents; Green Chem., vol. 10, Feb. 28, 2008, pp. 457-464, XP002724088, scheme 6; table 1.

* cited by examiner

*Primary Examiner* — Sudhakar Katakam
*Assistant Examiner* — Jennifer C Sawyer
(74) *Attorney, Agent, or Firm* — Dana Kolesar

(57) ABSTRACT

A method for preparing 1-adamantyltrimethylammonium hydroxide is disclosed. The method comprises reacting 1-adamantyldimethylamine with dimethyl carbonate to produce 1-adamantyltrimethylammonium methylcarbonate, which is then reacted with calcium hydroxide or magnesium hydroxide in the presence of water to produce 1-adamantyltrimethylammonium hydroxide.

14 Claims, No Drawings

METHOD OF MAKING A TEMPLATING AGENT

CROSS REFERENCE TO RELATED APPLICATION

This application claims priority benefit to U.S. Provisional Application No. 61/805,654 filed on Mar. 27, 2013, which is incorporated herein by reference.

FIELD OF THE INVENTION

The invention relates to a method for preparing 1-adamantyltrimethylammonium hydroxide.

BACKGROUND OF THE INVENTION

1-Adamantyltrimethylammonium hydroxide is useful as a templating agent in the production of zeolites. A standard route to prepare ammonium salts of organic amines, such as 1-adamantyltrimethylammonium hydroxide, includes an alkylation step in which the organic amine is reacted with an alkylating agent such as dialkyl sulfates or methyl iodide. For example, U.S. Pat. No. 8,252,943 discloses a process for preparing ammonium compounds by reacting compounds containing a double-bonded nitrogen atom with a dialkyl sulfate with participation of both alkyl groups of the dialkyl sulfate and, if appropriate, subjecting the resulting ionic compound containing sulfate anions to an anion exchange. Likewise, U.S. Pat. No. 8,163,951 teaches a process for preparing quaternary ammonium compounds, which comprises reacting compounds comprising an $sp^3$-hybridized nitrogen atom with a dialkyl sulfate or trialkyl phosphate and subjecting the resulting ammonium compound to an anion exchange. U.S. Pat. Appl. Pub. No. 2012/0010431 discloses a process for preparing 1-adamantyltrimethylammonium hydroxide that comprises reacting 1-adamantyldimethylamine with dimethyl sulfate to give 1-adamantyltrimethylammonium sulfate, which is then subjected to anion exchange with an ion exchanger loaded with OH ions. In addition, U.S. Pat. No. 4,859,442 describes at Example 1 the preparation of 1-adamantyltrimethylammonium hydroxide by alkylation of 1-adamantylamine with methyl iodide, followed by ion exchange of the iodide anions with an ion exchange resin.

As with any chemical process, it is desirable to attain still further improvements in processes for preparing 1-adamantyltrimethylammonium hydroxide. We have discovered a new method to produce 1-adamantyltrimethylammonium hydroxide with a high yield and reduced waste.

SUMMARY OF THE INVENTION

The invention is a method for preparing 1-adamantyltrimethylammonium hydroxide. The method comprises reacting 1-adamantyldimethylamine with dimethyl carbonate to produce 1-adamantyltrimethylammonium methylcarbonate, which is then reacted with calcium hydroxide or magnesium hydroxide in the presence of water to produce 1-adamantyltrimethylammonium hydroxide.

DETAILED DESCRIPTION OF THE INVENTION

The method of the invention comprises reacting 1-adamantyldimethylamine with dimethyl carbonate to produce 1-adamantyltrimethylammonium methylcarbonate. The 1-adamantyltrimethylammonium methylcarbonate is then reacted with calcium hydroxide or magnesium hydroxide in the presence of water to produce 1-adamantyltrimethylammonium hydroxide 1-adamantyldimethylamine may be produced by any known method. Preferably, the 1-adamantyldimethylamine is produced by first reacting 1-adamantylamine hydrochloride, formaldehyde, formic acid, and an inorganic base to produce 1-adamantyldimethylamine. The molar ratio of formaldehyde:1-adamantylamine hydrochloride is in the range of 2.1 to 2.4, and the molar ratio of formic acid:1-adamantylamine hydrochloride is in the range of 2.3 to 2.7.

This alkylation step is preferably performed neat, without the addition of solvents. Preferably, the alkylation step involves mixing the 1-adamantylamine hydrochloride and formic acid, followed by the addition of the inorganic base. Preferably, the inorganic base is a hydroxide, carbonate or bicarbonate of a Group I metal. More preferably, the inorganic base is sodium hydroxide.

The inorganic base may be added as a solid, but it is preferable to use an aqueous solution of the inorganic base (such as an aqueous solution of sodium hydroxide). The addition of inorganic base is preferably performed at a temperature less than 50° C., most preferably at ambient temperature. Formaldehyde is then preferably added to the alkylation reaction mixture. An aqueous, stabilized formaldehyde solution (for instance, stabilized with less than 10% methanol) is preferably utilized. Carbon dioxide gas evolution can be observed throughout the addition of formaldehyde to the alkylation reaction mixture. Typically, the alkylation reaction mixture is heated at a temperature greater than 50° C., more preferably from 60 to 95° C., for a period greater than about 0.25 hours. The reaction temperature may also be increased over the course of the reaction. For instance, the temperature may be initially maintained at a temperature in the range of 70 to 85° C., before increasing to a temperature in the range of 90 to 95° C. The reaction is typically performed from 1 to 24 hours.

The 1-adamantyldimethylamine is preferably isolated from the alkylation reaction mixture prior to the quaternization step. Preferably, the alkylation reaction mixture is cooled to a temperature less than 20° C., more preferably from 3 to 15° C., and the pH is adjusted to a pH greater than 13 by the addition of more inorganic base (such as sodium hydroxide). The cooled solution is preferably then subject to a solvent extraction step. The extraction solvent is preferably a $C_6$ or greater hydrocarbon, more preferably toluene. The weight ratio of hydrocarbon:solution is preferably from about 0.5:1 to about 3:1.

The solvent extraction is conveniently carried out at moderate temperatures. Suitable temperatures are in the range of about 10° C. to 100°, preferably 15° C. to 60° C. The extraction results in a hydrocarbon phase that comprises the 1-adamantyldimethylamine and an aqueous phase that contains methanol and salts. These two phases are easily separated, and the hydrocarbon phase may be stripped using a solvent stripper in order to remove the hydrocarbon from the 1-adamantyldimethylamine. The resulting 1-adamantyldimethylamine may be additionally filtered to remove any insoluble matter that remains.

In the method of the invention, 1-adamantyldimethylamine is reacted with dimethyl carbonate to produce 1-adamantyltrimethylammonium methylcarbonate in a quaternization step.

Preferably, the reaction of 1-adamantyldimethylamine and dimethyl carbonate is performed at elevated temperature and pressure, for example in an autoclave. Typically, the 1-adamantyldimethylamine/dimethyl carbonate reaction mixture is heated at a temperature of about 80° C. to about 200° C. for a period greater than about 0.25 hours (preferably less than about 48 hours) in a sealed vessel under autogenous pressure. More preferably, the reaction mixture is heated at a temperature range from about 100° C. to about 175° C., most preferably from about 120° C. to about 160° C. The reaction pressure may rise to about 100 to 180 psig. The reaction may be carried out in a batch, continuous, or semi-continuous manner using any appropriate type of reaction vessel or apparatus such as a stirred vessel or CSTR reactor. Preferably, the molar ratio of dimethyl carbonate:1-adamantyldimethylamine is in the range of 3 to 5.

After the reaction is complete, the 1-adamantyltrimethylammonium methylcarbonate is preferably recovered. Suitable recovery methods include filtration and washing, rotary evaporation, centrifugation, and the like. In a preferred embodiment, the reaction mixture is cooled to ambient temperature and a portion of the reaction mixture (preferably reducing the reaction volume by greater than 25%) is stripped to remove any methanol that might have formed. The remaining slurry may be further cooled to a temperature less than 10° C., and the -adamantyltrimethylammonium methylcarbonate product isolated by filtration and then washed with cold dimethyl carbonate. The white crystalline product can be further dried under vacuum to produce the final 1-adamantyltrimethylammonium methylcarbonate.

The 1-adamantyltrimethylammonium methylcarbonate is finally reacted with calcium hydroxide or magnesium hydroxide in the presence of water to produce 1-adamantyltrimethylammonium hydroxide. In addition to water, the reaction may be performed in the presence of other solvents, such as alcohols, but additional solvents are not required. At least one mole equivalent of water is utilized in comparison to the 1-adamantyltrimethylammonium methylcarbonate, but preferably an excess of water is used. A molar excess of calcium hydroxide or magnesium hydroxide to 1-adamantyltrimethylammonium methylcarbonate is preferred, more preferably the molar ratio of calcium hydroxide (magnesium hydroxide):1-adamantyltrimethylammonium methylcarbonate is in the range of 1.05 to 1.75.

Preferably, the 1-adamantyltrimethylammonium methylcarbonate/calcium hydroxide (magnesium hydroxide) reaction mixture is heated at an elevated temperature, preferably at reflux. The methanol produced is slowly distilled off until the vapor temperature is constant.

The 1-adamantyltrimethylammonium hydroxide product is preferably isolated from the resulting calcium (magnesium) carbonate and excess calcium (magnesium) hydroxide. Preferably, the reaction mixture is cooled to a temperature less than 15° C., and the precipitated calcium or magnesium salts (e.g., $CaCO_3$ and $(Ca(OH)_2)$ are filtered off. The filter cake is preferably washed with additional water and both the mother and wash filtrates may be combined. The 1-adamantyltrimethylammonium hydroxide may be used as an aqueous solution or may be further isolated from the water by drying, stripping, or the like.

The can be used as a templating agent for the production of zeolites. Zeolite synthesis is well-known in the art, and generally consists of reacting a silicon source, an aluminum source, (plus other metal sources if desired), and the 1-adamantyltrimethylammonium hydroxide templating agent at a temperature and for a time sufficient to form a molecular sieve. Typical silicon sources include colloidal silica, fumed silica, silicon alkoxides, and mixtures thereof. Typical aluminum sources include sodium aluminate, aluminum hydroxide, aluminum isopropoxide, aluminum sulfate, and aluminum nitrate.

The zeolite synthesis is typically performed in the presence of water. Other solvents such as alcohols may also be present. After the reaction mixture is formed, it is reacted at a temperature and a time sufficient to form a molecular sieve. Typically, the reaction mixture is heated at a temperature of about 100° C. to about 250° C. for a period greater than about 0.25 hours (preferably less than about 96 hours) in a sealed vessel under autogenous pressure. The reaction may be carried out in a batch, continuous, or semi-continuous manner using any appropriate type of reaction vessel or apparatus such as a stirred vessel or CSTR reactor. After the reaction is complete, the zeolite is recovered.

As synthesized, the zeolite will contain some of the templating agent in the pores. Any suitable method to remove the templating agent may be employed. The template removal is typically performed by a high temperature heating in the presence of an oxygen-containing gas, such as air or a mixture of oxygen and an inert gas. Preferably, the zeolite is heated at temperatures greater than 250° C. to remove the templating agent. Temperatures of from about 275° C. to about 800° C. are preferred.

The following examples merely illustrate the invention. Those skilled in the art will recognize many variations that are within the spirit of the invention and scope of the claims.

Example 1

1-Adamantyltrimethylammonium Hydroxide Preparation

1-Adamantanyldimethylamine Synthesis:

1-Adamantanamine hydrochloride, 99% (500 g, 2.66 mol) is charged into a reaction flask under a nitrogen atmosphere, followed by formic acid, 97% (306 g, 6.65 mol). The reaction mixture is stirred at room temperature, then sodium hydroxide 32% w/w aqueous solution (326 g, 2.61 mol) is added over 30 minutes at a temperature less than 50° C., after which the reaction mixture is heated to 75-80° C. Formaldehyde, 37% w/w aqueous solution stabilized with 7-8% methanol (475 g, 5.86 mol) is then added to the reaction mixture. Gas (carbon dioxide) evolution is observed throughout the addition and the reaction temperature is maintained at 75-80° C. throughout.

The reactor contents temperature is increased to bring the reaction mixture to 95° C. over 30 minutes and is maintained at this temperature for the next 3 hours. GC analysis shows >97% conversion to the dimethyl amine. The reaction mixture is then cooled to 5° C. and sodium hydroxide 32% w/w aqueous solution (200 g) is added to adjust the reaction mixture to pH 14. To this stirred reaction mixture, toluene, 99% (1,250 mL) is added and the reaction mixture is allowed to settle into two phases. The upper organic layer is separated and stripped free of solvent to give a clear yellow liquid which is then filtered to remove insoluble matter. The overall yield of 1-adamantanyldimethylamine is 472 grams (97.5% of theory) with GC area % about 96.2% with residual 1.8% toluene.

Adamantyltrimethylammonium Methylcarbonate Synthesis:

1-Adamantanyldimethylamine (500 g, 2.79 mol) and dimethyl carbonate (1000 g, 11.1 mol) are charged into an autoclave, and the reactor contents are heated at 140° C. for 8 hours with the reactor pressure rising to 140 psig (965 kPa). After cooling to ambient temperature and venting any residual pressure, the contents of the autoclave (a mobile slurry) are transferred to a rotary evaporator and solvent stripped off to reduce the volume by half which will remove any methanol that might have been formed. The remaining slurry is cooled to 0° C. and the product isolated by filtration on a Nutsche filter. The filter cake is washed with cold dimethyl carbonate (500 mL), followed by another cold dimethyl carbonate (200 mL) wash, before drying under vacuum to give a yield of 668 grams of an off-white crystalline solid (89% of theory). H-NMR analysis is consistent with structure.

1-Adamantyltrimethylammonium Hydroxide Synthesis:

Adamantyltrimethylammonium methylcarbonate (383 g, 1.42 mol) is added to water (1000 mL), followed by addition of calcium hydroxide (148 g, 2.0 mol). This addition is exothermic. The reaction mixture is then heated to reflux and the methanol produced is slowly distilled off until the vapor temperature is constant. The reaction mixture is then cooled slowly to 10° C. and the precipitated calcium carbonate and excess calcium hydroxide are filtered off on a Nutsche filter. The filter cake is washed with water (200 mL) and both the mother and wash filtrates are combined. The 1-adamantyltrimethylammonium hydroxide product yield is 1284 grams of solution with assay 20.2% w/w.

We claim:

1. A method for preparing 1-adamantyltrimethylammonium hydroxide, comprising:
   (a) reacting the 1-adamantyldimethylamine with dimethyl carbonate to produce 1-adamantyltrimethylammonium methylcarbonate, wherein the molar ratio of dimethylcarbonate:1-adamantyldimethylamine is in the range of 3 to 5; and
   (b) reacting the 1-adamantyltrimethylammonium methylcarbonate with calcium hydroxide or magnesium hydroxide in the presence of a water to produce 1-adamantyltrimethylammonium hydroxide.

2. The method of claim 1 wherein the molar ratio of calcium hydroxide or magnesium hydroxide:1-adamantyltrimethylammonium methylcarbonate is in the range of 1.05 to 1.75.

3. The method of claim 1 wherein the reaction of 1-adamantyltrimethylammonium methylcarbonate with calcium hydroxide or magnesium hydroxide in the presence of water is performed at reflux.

4. The method of claim 1 wherein the reaction of 1-adamantyldimethylamine with dimethyl carbonate is performed at a temperature in the range of 120-160° C.

5. The method of claim 1 wherein the 1-adamantyltrimethylammonium methylcarbonate is reacted with calcium hydroxide.

6. A method for preparing 1-adamantyltrimethylammonium hydroxide, comprising:
   (a) producing 1-adamantyldimethylamine by reacting 1-adamantylamine hydrochloride, formaldehyde, formic acid, and an inorganic base to produce 1-adamantyldimethylamine, wherein the molar ratio of formaldehyde:1-adamantylamine hydrochloride is in the range of 2.1 to 2.4 and the molar ratio of formic acid:1-adamantylamine hydrochloride is in the range of 2.3 to 2.7;
   (b) reacting the 1-adamantyldimethylamine with dimethyl carbonate to produce 1-adamantyltrimethylammonium methylcarbonate, wherein the molar ratio of dimethyl carbonate:1-adamantyldimethylamine is in the range of 3 to 5; and
   (c) reacting the 1-adamantyltrimethylammonium methylcarbonate with calcium hydroxide or magnesium hydroxide in the presence of a water to produce 1-adamantyltrimethylammonium hydroxide.

7. The method of claim 6 wherein the inorganic base is a hydroxide, a carbonate or a bicarbonate of a Group I metal.

8. The method of claim 6 wherein the inorganic base is sodium hydroxide.

9. The method of claim 6 wherein the reaction of 1-adamantylamine hydrochloride, formaldehyde, formic acid, and the inorganic base is performed by mixing 1-adamantylamine hydrochloride and formic acid, followed by the addition of the inorganic base, and then adding the formaldehyde.

10. The method of claim 6 wherein the 1-adamantyltrimethylammonium methylcarbonate is reacted with calcium hydroxide.

11. The method of claim 6 wherein the molar ratio of calcium hydroxide or magnesium hydroxide:1-adamantyltrimethylammonium methylcarbonate is in the range of 1.05 to 1.75.

12. The method of claim 6 wherein the reaction of 1-adamantyltrimethylammonium methylcarbonate with calcium hydroxide or magnesium hydroxide in the presence of water is performed at reflux.

13. The method of claim 6 wherein the reaction of 1-adamantyldimethylamine with dimethyl carbonate is performed at a temperature in the range of 120-160° C.

14. The method of claim 6 wherein the 1-adamantyltrimethylammonium methylcarbonate is reacted with calcium hydroxide.

* * * * *